(12) United States Patent
Hodgson-Zingman et al.

(10) Patent No.: US 10,987,516 B2
(45) Date of Patent: Apr. 27, 2021

(54) SYSTEMS AND METHODS FOR CARDIOVASCULAR CONDITIONING

(71) Applicant: UNIVERSITY OF IOWA RESEARCH FOUNDATION, Iowa City, IA (US)

(72) Inventors: Denice Marie Hodgson-Zingman, Iowa City, IA (US); Leonid Vladimir Zingman, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 15/764,597

(22) PCT Filed: Sep. 30, 2016

(86) PCT No.: PCT/US2016/054827
§ 371 (c)(1),
(2) Date: Mar. 29, 2018

(87) PCT Pub. No.: WO2017/059271
PCT Pub. Date: Apr. 6, 2017

(65) Prior Publication Data
US 2018/0214690 A1 Aug. 2, 2018

Related U.S. Application Data

(60) Provisional application No. 62/235,024, filed on Sep. 30, 2015.

(51) Int. Cl.
*A61N 1/362* (2006.01)
*A61N 1/365* (2006.01)
(Continued)

(52) U.S. Cl.
CPC ........... *A61N 1/365* (2013.01); *A61N 1/3627* (2013.01); *A61N 1/36514* (2013.01);
(Continued)

(58) Field of Classification Search
CPC ...... A61N 1/362; A61N 1/3627; A61N 1/365; A61N 1/36514; A61N 1/36521;
(Continued)

(56) References Cited

U.S. PATENT DOCUMENTS 4,574,807 A * 3/1986 Hewson ............... A61N 1/0517
607/27
4,884,575 A * 12/1989 Sanders ................ A61N 1/362
607/30

(Continued)

FOREIGN PATENT DOCUMENTS

WO PCT/US2016/054827 9/2016

OTHER PUBLICATIONS

U.S. Appl. No. 62/235,024, filed Sep. 30, 2015, Denice M. Hodgson-Zingman (University of Iowa Research Foundation).
(Continued)

*Primary Examiner* — Eugene T Wu
(74) *Attorney, Agent, or Firm* — Ballard Spahr LLP

(57) ABSTRACT

An example system has a pulse generator configured to deliver a first series of electrical signals to a right atrium of a heart. The first series of electrical signals can increase a first heart rate toward a target heart rate. The system can have a monitoring device configured to retrieve physiological data from a user of the system while the heart is receiving the first series of electrical signals. The system can have a controller configured to determine whether a physiological parameter has met a physiological threshold based on the physiological data. If the physiological threshold has been met, the controller can modify the first series of electrical
(Continued)

signals to a second series of electrical signals that restores the physiological parameter to an acceptable level.

20 Claims, 10 Drawing Sheets

(51) Int. Cl.
 *A61N 1/372* (2006.01)
 *A61N 1/37* (2006.01)
(52) U.S. Cl.
 CPC ....... *A61N 1/3702* (2013.01); *A61N 1/37235* (2013.01); *A61N 1/3621* (2013.01); *A61N 1/37282* (2013.01)
(58) Field of Classification Search
 CPC ............ A61N 1/36564; A61N 1/36572; A61N 1/36585; A61N 1/37235; A61N 1/37241; A61N 1/385; A61B 5/02028; A61B 5/0205; A61B 5/021; A61B 5/029; A61B 5/0452; A61B 5/0468; A61B 5/0472
 See application file for complete search history.

(56) References Cited

U.S. PATENT DOCUMENTS

| | | | |
|---|---|---|---|
| 4,884,576 A | 12/1989 | Alt | |
| 5,919,209 A * | 7/1999 | Schouten | A61N 1/362 607/2 |
| 7,447,544 B1 | 11/2008 | Kroll | |
| 8,483,826 B2 * | 7/2013 | Zielinski | A61N 1/3627 607/15 |
| 8,983,600 B2 * | 3/2015 | Shuros | A61N 1/368 607/14 |
| 2004/0260348 A1 * | 12/2004 | Bakken | A61N 1/365 607/9 |
| 2006/0122650 A1 * | 6/2006 | Warman | A61N 1/3622 607/14 |
| 2008/0114408 A1 * | 5/2008 | Shuros | A61N 1/3627 607/11 |
| 2008/0177194 A1 * | 7/2008 | Zhang | A61N 1/365 600/513 |
| 2008/0221636 A1 * | 9/2008 | Pastore | A61N 1/3627 607/18 |
| 2008/0234774 A1 * | 9/2008 | Baynham | A61N 1/3627 607/18 |
| 2009/0082823 A1 * | 3/2009 | Shuros | A61N 1/3627 607/17 |
| 2009/0234240 A1 | 9/2009 | Kuenzler et al. | |
| 2010/0305648 A1 * | 12/2010 | Arcot-Krishnamurthy | A61N 1/3627 607/21 |
| 2014/0277256 A1 * | 9/2014 | Osorio | A61N 1/36146 607/45 |

OTHER PUBLICATIONS

International Search Report and Written Opinion dated Feb. 3, 2017 by the International Searching Authority for Patent Application No. PCT/US2016/054827, which was filed on Sep. 30, 2016 and published as WO 2017/059271 on Apr. 6, 2017 (Inventor—Hodgson-Zingman et al.; Applicant—University of Iowa Research Foundation) (9 pages).

International Preliminary Report on Patentability dated Apr. 3, 2018 by the International Searching Authority for Patent Application No. PCT/US2016/054827, which was filed on Sep. 30, 2016 and published as WO 2017/059271 on Apr. 6, 2017 (Inventor—Hodgson-Zingman et al.; Applicant—University of Iowa Research Foundation) (7 pages).

* cited by examiner

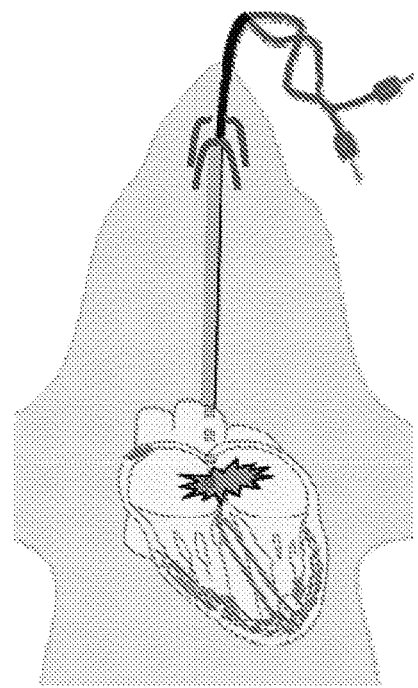
FIG. 5
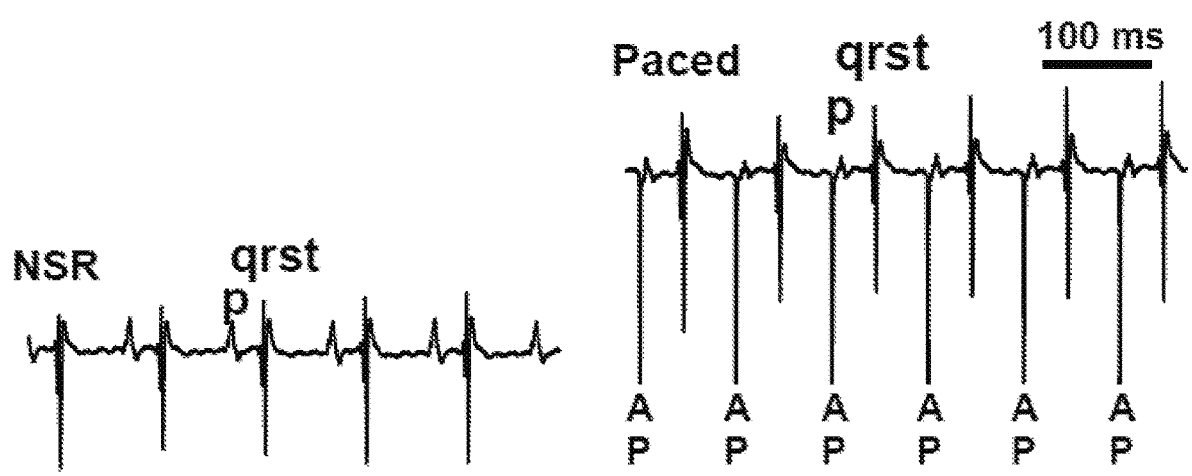
FIG. 6A
FIG. 6B

SYSTEMS AND METHODS FOR CARDIOVASCULAR CONDITIONING

CROSS-REFERENCE TO RELATED APPLICATIONS

This application is a U.S. National Phase Application of International Patent Application No. PCT/US2016/054827, filed Sep. 30, 2016, which claims priority to U.S. Provisional Patent Application No. 62/235,024, filed Sep. 30, 2015, both of which are herein incorporated by reference in their entireties.

BACKGROUND

Heart failure is a public health problem affecting millions of people worldwide. Despite considerable progress in the treatment of heart failure, heart failure is still associated with high morbidity. As such, identifying new preventions and treatments for heart failure is one of the greatest challenges in medicine. Biventricular (coordinated left and right ventricle) pacing to improve ventricular contractile synchrony is among the most successful recent advances in heart failure therapy. This technique leads to improved quality of life, clinical indicators of heart failure severity, and survival thereby illustrating the power of pacing to beneficially remodel dysfunctional myocardium. However, biventricular pacing requires technically challenging implantation of specialized hardware and is thus burdened by higher costs and complication rates when compared to standard right heart only pacing systems. Further, it is only appropriate for a small subset of heart failure patients who have severe ventricular dysfunction and dyssynchrony. Other currently utilized pacing systems serve to treat or prevent inadequate heart rates or terminate abnormal rhythms but are not intended to improve the condition or function of diseased myocardium. Approaches have been proposed that purposely stress the heart through pacing at increased heart rates combined with intentional induction of ventricular dyssynchrony, such as by right ventricular pacing, in order to initiate beneficial myocardial conditioning/remodeling. However, the energetically and hemodynamically unfavorable atrio-ventricular and/or interventricular dyssynchrony with such an approach limits its tolerability and counteracts beneficial effects thereby ultimately restricting its therapeutic utility. As such, these pacing approaches lack proper controls and feedback to efficiently condition or "reverse remodel" the myocardium to improve myocardial function, heart failure symptoms and other related heart disease outcomes.

The present disclosure describes a pacing intervention that overcomes these and other shortcomings of the prior art. The described invention is based on the principle of "exercise-inspired" pacing. Specifically, the powerful benefits of exercise for steering outcomes in cardiovascular disease, particularly heart failure, are increasingly appreciated. However, patients with cardiovascular disease face many impediments to adequate exercise. The magnitude and duration of heart rate acceleration with exercise is commonly viewed as a predictive indicator for cardiovascular benefit. However, based on the data provided herein, intermittent acceleration of heart rate, when isolated from other aspects of exercise by pacing, can act as an independent effector of beneficial myocardial conditioning when it is delivered in an optimally physiologic fashion through use of feedback controls that support myocardial efficiency and cardiac output.

SUMMARY

The disclosed methods and systems relate to heart pacing to improve cardiovascular conditioning. An example system can comprise a pulse generator configured to deliver a first series of electrical signals to of a heart. The first series of electrical signals can increase a first heart rate toward a target heart rate. The system can comprise a monitoring device configured to retrieve physiological data from a user of the system while the heart is receiving the first series of electrical signals. The system can comprise a controller configured to determine whether a physiological parameter has met a physiological threshold based on the physiological data. If the physiological threshold has been met, the controller can modify the first series of electrical signals to a second series of electrical signals that restores the physiological parameter to an acceptable level.

In an example method, a first series of electrical signals can be delivered to the right atrium of the heart of a user. The first series of electrical signals can increase a first heart rate toward a target heart rate. Physiological data of the user can be retrieved during delivery of the first series of electrical signals. The heart can be at a second heart rate greater than the first heart rate when the physiological data is retrieved. The method can comprise a step of determining whether a physiological parameter has met a physiological threshold based on the physiological data. If the physiological threshold has been met, the first series of electrical signals can be modified to a second series of electrical signals that restores the physiological parameter to an acceptable level. If the physiological threshold has not been met, the first series of electrical signals can be delivered until the target heart rate is met.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems.

FIG. 5 is a schematic representation of an exemplary pacing intervention system as disclosed herein. As shown, selective atrial pacing can be achieved by a trans-esophageal bipolar pacing catheter.

FIG. 6A shows an exemplary electrocardiogram in an anesthetized mouse during normal sinus rhythm ("NSR").
FIG. 6B shows an exemplary electrocardiogram in an anesthetized mouse during pacing intervention. The "p" represents an atrial electrogram, "qrst" represents a ventricular electrogram, and "AP" represents an atrial pacing stimulus artifact.

DETAILED DESCRIPTION

Figure 1A:
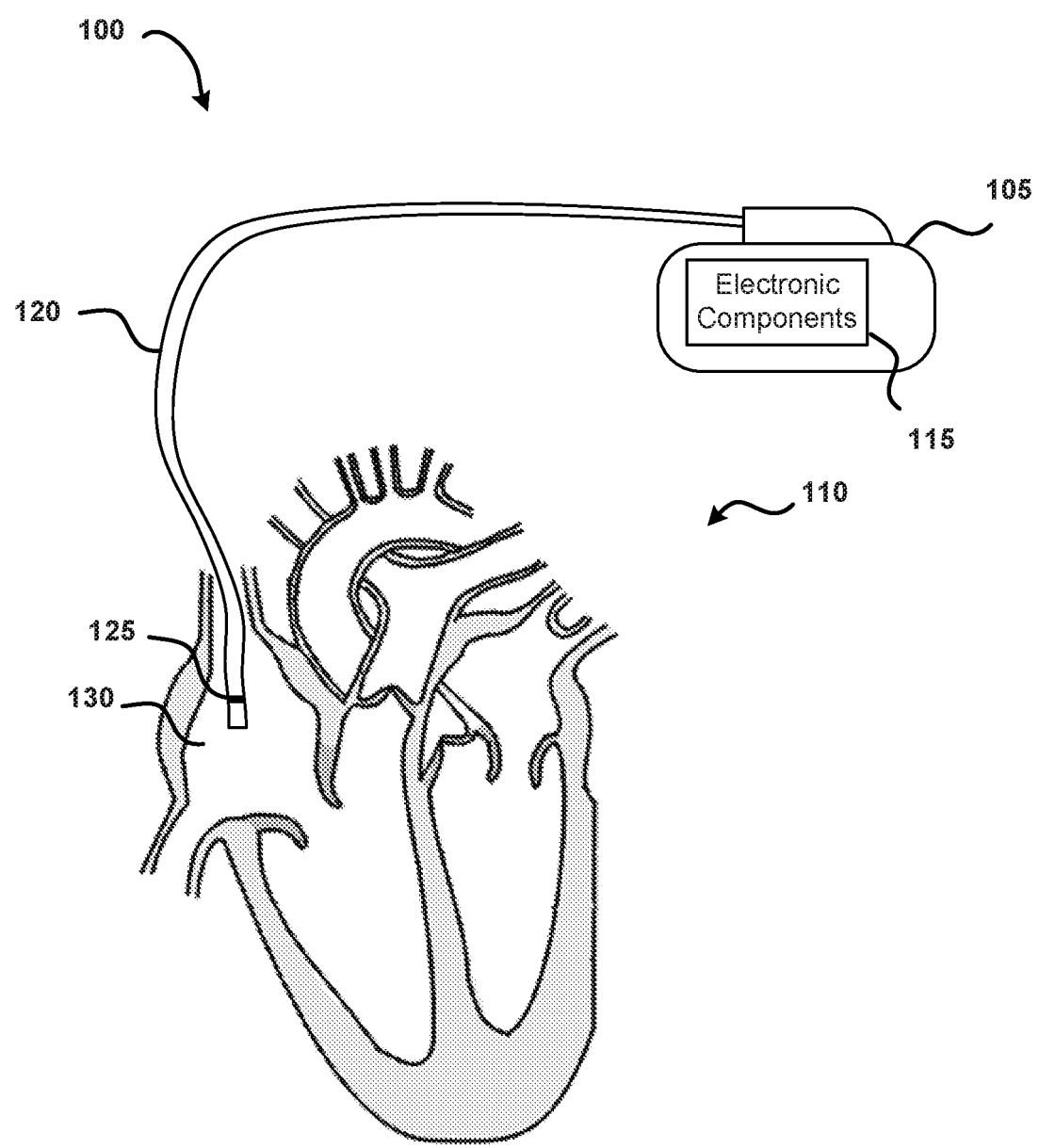
FIG. 1A is a block diagram illustrating an example system.

Before the present methods and systems are disclosed and described, it is to be understood that the methods and systems are not limited to specific methods, specific components, or to particular configurations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

When used herein to describe atrio-ventricular or interventricular synchrony, the term "optimal" refers to conditions in which atrio-ventricular or interventricular synchrony is within an acceptable range that achieves the beneficial effects of the pacing methods disclosed herein. Thus, an "optimal" atrio-ventricular synchrony can include a perfectly normal (1:1) synchrony and atrioventricular delay (120-200 msec PR interval on the body surface electrocardiogram [ECG]), as well as other conditions where the synchrony is not perfectly normal (not 1:1 and/or shortened or prolonged PR interval), and an optimal interventricular synchrony can include a perfectly normal morphology and duration (<100 msec) of the QRS complex on ECG, as well as other conditions where the synchrony is not perfectly normal (>100 msec and/or atypical QRS morphology on ECG) provided the effectiveness of the disclosed pacing methods are not diminished. For example and without limitation, it is contemplated that an atrio-ventricular synchrony ratio ranging from about 0.8:1 to about 1.2:1 and/or a PR interval on ECG ranging from 100-240 msec can be an optimal atrio-ventricularrelationship, and a QRS duration <130 msec with an interventricular conduction delay or biventricular paced morphology on ECG can represent optimal interventricular synchrony. However, it is contemplated that other synchrony ratios and indicators can be used to maintain the effectiveness of the disclosed pacing methods.

As used herein, the term "atrio-ventricular synchrony" refers to a heart activation sequence in which first the atria then (after an appropriate delay) the ventricles contract. Such synchrony is manifested by the ratio of atrial to ventricular contractions (specifically, in normal synchrony, a 1:1 synchrony ratio refers to the condition when each contraction of the atria is followed by a single contraction of the ventricles) as well as the sequence and timing of such contractions (specifically the contraction of the ventricles occurring within a specified time period after the contraction of the atria). As used herein, the term "interventricular synchrony" refers to the coordinated, simultaneous contraction of the right and left ventricles. Methods for determination of atrio-ventricular and interventricular synchrony include, but are not limited to, the timing of atrial and ventricular electrical activity on body surface electrocardiogram (ECG), other electrograms obtained without direct contact to the heart such as subcutaneous monitors, intracardiac electrograms such as those measured by electrodes placed in or on the heart, visual or acoustic imaging of cardiac contractions such as obtained by echocardiography, hemodynamic measurements of cardiac contractions such as obtained by pressure or volume sensors within the cardiac chambers or assessment of cardiac chamber filling and/or ejection by the Doppler technique.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Systems and methods of pacing the heart to induce favorable remodeling ("reverse remodeling") of the cardiac muscle to improve function and resistance to injury in subjects (optionally, for example, subjects with heart disease) are described herein. In an aspect, a pacing device can be used to intermittently escalate the heart rate of a subject above a resting rate by pacing the right atrium. The subject can be a human or an animal. In an aspect, the subject can be a human patient with one or more heart conditions. The pacing device can pace the right atrium by sending a series of electrical signals to the right atrium. During pacing, a monitoring device coupled to one or more sensors can provide feedback of physiological data to the pacing device. The pacing device can use the physiological data to determine whether a physiological parameter has met a physiological threshold. If the physiological threshold has been met, the series of electrical signals can be modified to restore the physiological parameter to an acceptable threshold. For example, the pacing device can help ensure a stroke volume threshold, a cardiac output threshold, a systolic blood pressure threshold, an oxygen saturation threshold, an arrhythmia threshold, a dyssynchrony threshold that indicates a loss of 1:1 or other optimal atrio-ventricular conduction/atrio-ventricular synchrony, an interventricular electrical activation pattern threshold, a patient-activated symptom threshold, combinations thereof, and other thresholds of physiological parameters are satisfied.

According to systems and methods in the present disclosure, the feedback can be used to augment cardiac output (e.g., by heart rate and force-frequency effects) and thereby induce molecular remodeling mechanisms, such as, for example and without limitation, upregulation of cardioprotective ion channels and mitochondrial respiratory components, that improve myocardial energetics and function. Contraction force can increase with heart rate acceleration over typical physiological ranges (e.g. force-frequency, Treppe, or Bowditch effect) and beneficial cardiovascular conditioning is supported by repeated episodes of increased heart rate and/or contraction force interspersed with rest, as occurs with various types of exercise, so long as optimally energetically efficient contraction, as indicated by physiologic atrio-ventricular and interventricular synchrony, combined with additional markers of hemodynamic stability, are maintained. In exemplary aspects, it is contemplated that the disclosed systems and methods can be used to induce beneficial molecular changes that tend to restore normal chamber dimensions and thickness, contractile force, relaxation, energy utilization, electrical stability and/or stress resistance. Such changes can include, for example and without limitation, normalization of calcium handling pathways such as by modified expression and function of sarco/endoplasmic reticulum calcium-ATPase (SERCA), cardioprotective/metabolic pathways such as by modified of expression or function of ATP-sensitive potassium channels and/or changes in mitochondrial biogenesis as reflected by expression of regulatory proteins such as optic atrophy 1 (OPA1) and peroxisome proliferator-activated receptor gamma coactivator 1-alpha (PGC1-alpha).

In an aspect, the monitoring device can ensure normal or near-normal atrio-ventricular and interventricular electrical activation. Grossly abnormal atrio-ventricular and interventricular activation patterns, either intrinsic or induced by pacing, can result in pathologic myocardial remodeling and therefore would be expected to counteract beneficial effects of intermittent heart rate acceleration. The methods and systems herein can eliminate pacing that causes such malignant stress or dyssynchrony and rather provide pacing that contributes to beneficial and optimally synchronous episodic heart rate acceleration. The methods and systems disclosed herein can be used to improve heart failure symptoms and outcomes, reduce heart injury during surgery or coronary angioplasty/stenting, improve exercise tolerance, and reduce angina pain in people with heart disease. The methods and systems herein can also be used in conjunction with existing pacing devices that can be reprogrammed to perform the methods described herein.

FIG. 1A is a block diagram of an example system 100 for cardiovascular conditioning. In an aspect, a pacing device 105 can be in electrical communication with a heart 110. In an aspect, the pacing device 105 can be any permanent or temporary, implantable or wearable, internal or external cardiac device that can stimulate the heart to contract (e.g., a permanent or temporary pacemaker, implantable cardioverter defibrillator (ICD), and the like). In an aspect, the pacing device 105 can be any existing programmable pacing device 105. In an aspect, the pacing device 105 can comprise electronic components 115, at least one lead 120, and at least one electrode 125. The electronic components 115 can comprise a programmable electronic controller that causes a pulse generator to send electrical signals in response to lapsed time intervals and/or sensed electrical activity. The electrical signals can be sent via the at least one lead 120 to the at least one electrode 125 in order to excite myocardial tissue. In an aspect, the at least one electrode 125 can be disposed in the right atrium 130, His bundle, esophagus or other location in which pacing of the heart would not automatically create interventricular dyssynchrony. In an aspect, the at least one electrode 125 can be used to sense cardiac electrical activity through one or more sensing channels and received by a monitoring device which can be incorporated into the electronic components 115 of the pacing device 105.

Figure 1B:
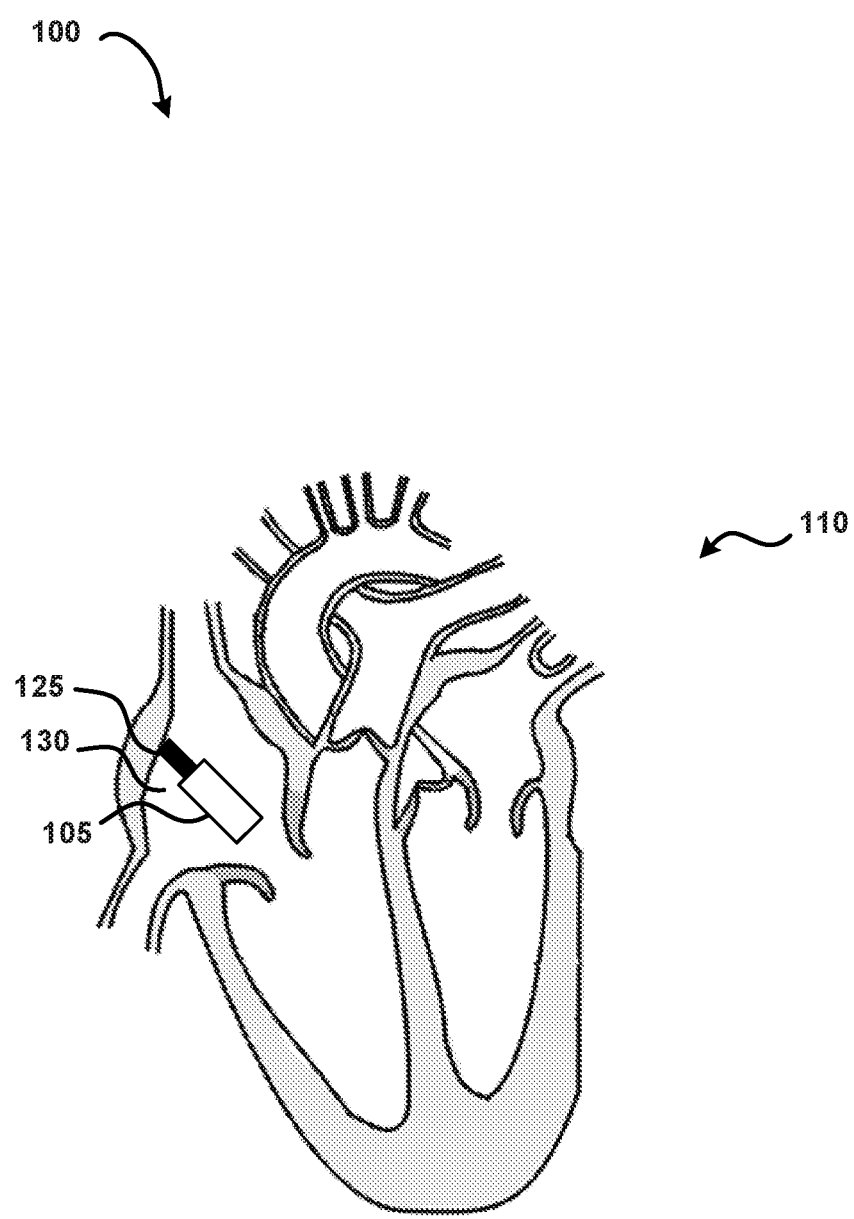
FIG. 1B is a block diagram illustrating another aspect of the example system.

FIG. 1B illustrates another aspect of the example system 100, for cardiovascular conditioning. In an aspect, the pacing device 105 can be a pacing device that is leadless. The pace device 105, if leadless, can be attached like a tag directly to the heart chamber the pacing device 105 is meant to pace, or to another structure from which cardiac pacing can be delivered such as esophagus, so no lead, such as lead 120 of FIG. 1A, is required.

In an aspect, the pacing device 115 can be used to perform cardiovascular conditioning. In an aspect, the pacing device can deliver a first series of electrical signals to the heart 110 of a user. The first series of electrical signals can increase the first heart rate toward a target heart rate for a target duration. The pacing device 105 can retrieve physiological data of the user before or during delivery of the first series of electrical signals. The pacing device 105 can comprise a monitoring device that can retrieve the physiological data and/or the pacing device 105 can be in communication with the monitoring device that transmits the physiological data to the pacing device 105. The heart 110 can be at a second heart rate greater than the first heart rate when the physiological data is retrieved. The pacing device 105 can determine whether a physiological parameter has met a physiological threshold based on the physiological data. If the physiological threshold has been met, the first series of electrical signals can be modified to a second series of electrical signals that restores the physiological parameter to an acceptable physiological threshold. For example, the pacing device 105 can help ensure that a stroke volume threshold, a cardiac output threshold, a systolic blood pressure threshold, an oxygen saturation threshold, an arrhythmia threshold, a dyssynchrony threshold that indicates a loss of 1:1 or other optimal atrio-ventricular conduction/atrio-ventricular synchrony, a interventricular electrical activation pattern threshold, a patient-activated symptom threshold, combinations thereof, or other physiological thresholds of physiological parameters are satisfied. If the physiological threshold has not been met, the first series of electrical signals can be delivered to the heart 110 by the pacing device 105 until the target heart rate is met for the target duration.

The electrical signals disclosed herein refer to pacing stimuli that are designed to induce contraction of a targeted cardiac chamber. The characteristics of the electrical signals can include, for example and without limitation, their frequency of delivery (paced rate) and the timing of their delivery with respect to other signals such as sensed cardiac electrical activity from the cardiac chamber targeted for pacing or from another location to which synchronization of contraction is targeted by adjustment of the timing and location of the pacing stimulus relative to the sensed signal. The procedures for varying pacing stimuli parameters are well-known and are not described herein in detail. However, it is understood that one or more parameters of the electrical signals can be selectively controlled or adjusted to achieve a desired result in a patient as further disclosed herein. Typically, the pacing stimuli disclosed herein comprise electrical signals that are of sufficient strength and duration to cause the heart to beat. In exemplary aspects, the electrical signals can comprise a direct current (DC) monophasic or biphasic pulse. However, in other exemplary aspects, it is contemplated that the electrical signals can comprise an alternating current (AC) pulse. The optimal pulse amplitude and duration for each electrical signal can depend upon the location and characteristics of the electrode, the heart tissue, and the interface between the electrode and the heart tissue. For example, it is contemplated that an electrode in direct contact with the right atrium wall of a heart can require a monophasic pulse amplitude of between about 0.1 and about 10 Volts, and a pulse duration between about 0.1 and about 2 msec, to cause the atrium to contract. In use, it is contemplated that the frequency of cardiac contractions can be determined by the frequency of such pacing pulses. A practical range of frequencies of pacing stimuli can range from about 50 pulses per minute to about 150 pulses per minute.

Although disclosed herein as electrical signals, it is contemplated that the pacing stimuli can comprise non-electrical means that can be used to pace the heart in accordance with the methods disclosed herein. For example, it is contemplated that the non-electrical means can comprise a generator, actuator, transmitter, or the like that is capable of generating one or more types of stimulation that are configured to cause contraction of the heart. For example, it is contemplated that the non-electrical means can comprise a mechanical actuator as is known in the art that is capable of delivering a mechanical stimulus that is configured to initiate, or cooperate with another stimulus (e.g., electrical) to initiate, contraction of the heart. In another example, the non-electrical means can comprise a conventional sonic- or radio-wave generator as is known in the art that is capable of delivering a sonic or radio wave to initiate, or cooperate with another stimulus (e.g., electrical) to initiate, contraction of the heart. In another exemplary aspect, the non-electrical means can comprise a conventional light source that is capable of delivering light or a light beam to initiate, or cooperate with another stimulus (e.g., electrical) to initiate, contraction of the heart. In still another exemplary aspect, the non-electrical means can comprise a conventional heat source that is capable of delivering heat to initiate, or cooperate with another stimulus (e.g., electrical) to initiate, contraction of the heart.

Figure 2:
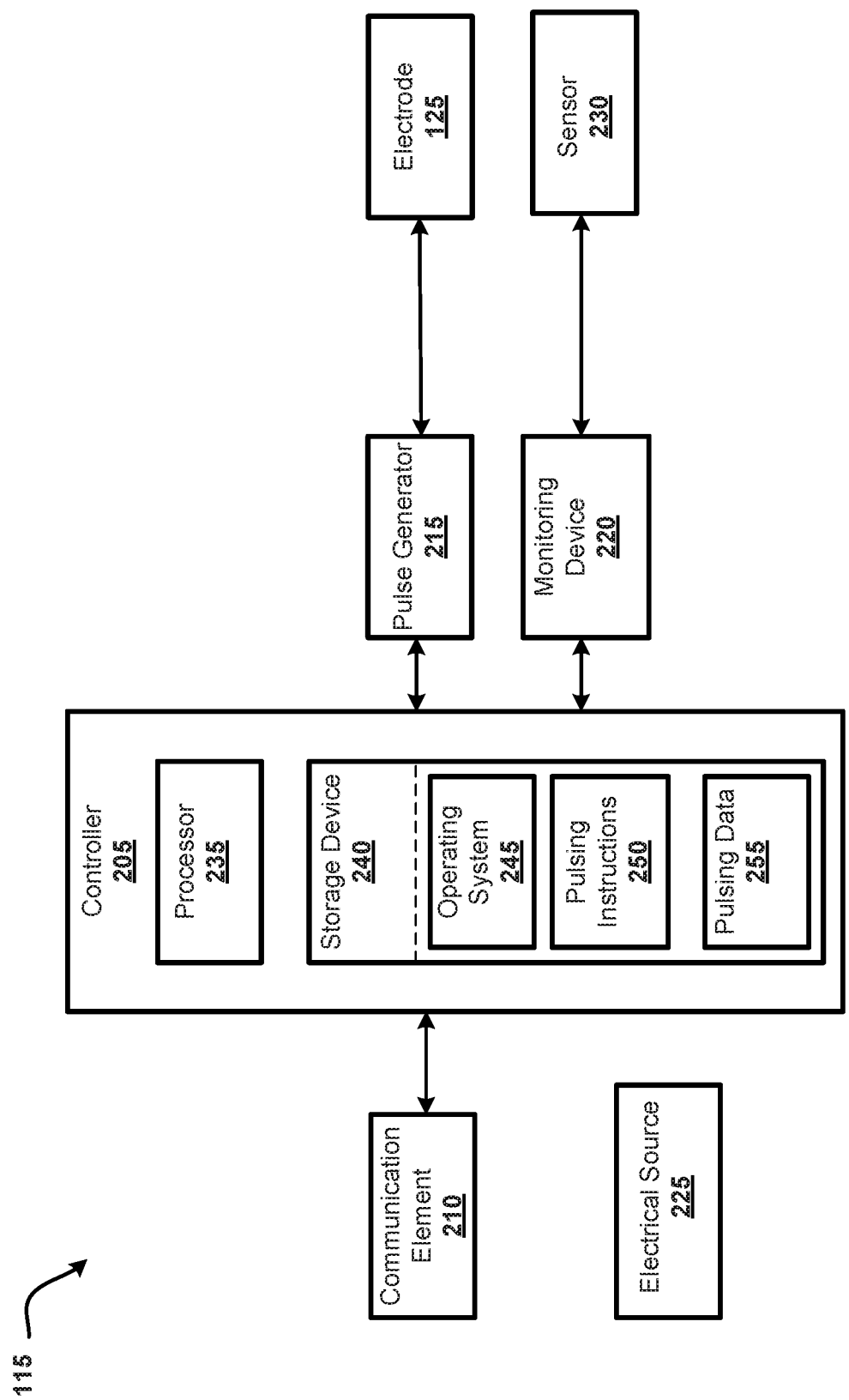
FIG. 2 is a block diagram illustrating an example system.

FIG. 2 illustrates the electronic components 115 of the pacing device 105, according to various aspects. In an aspect, the electronic components 115 can comprise a controller 205, a communication element 210, a pulse generator 215, a monitoring device 220, and an electrical source 225 (e.g., battery) that supplies electricity to all of the electronic components 115. In an aspect, the controller 205 can comprise a processor 235, and a storage device 240, which can comprise an operating system 245, pulsing instructions 250, and pulsing data 255. In an aspect, the controller 205 can control the overall operation of the pacing device 105 in accordance with the pulsing instructions 250 stored in the storage device 240. In an aspect, the controller 205 can comprise timing circuitry such as external clocks for implementing timers used to measure lapsed intervals and schedule events.

In an aspect, the communication element 210 can be in communication with the controller 205 and can allow the controller 205 to communicate with an external device such as an external computing device used to program the pulsing instructions 250, transfer pulsing data 255, combinations thereof, and the like. In an aspect, the communication element 210 can allow the controller 205 to communicate with a remote monitoring device that is external to the pacing device 105. The communication element 210 can use any wired and/or wireless communication protocols.

In an aspect, the pulse generator 215 can be in communication with the controller 205. In an aspect, the controller 205 can signal the pulse generator to deliver a series of electrical signals to the at least one electrode 125 disposed in or near the heart. The pulse generator 215 can also comprise a shocking pulse generator for delivering a defibrillation shock via the at least one electrode 125. In an aspect, the pulse generator 215 can be an existing pulse generator that can be reprogrammed to practice the disclosed methods.

In an aspect, the monitoring device 220 can be disposed within the pacing device 105 as part of the electronic components 115 and/or separately from the electronic components as a standalone device that communicates with the controller 205 via the communication element 210 or other computing device that is in communication with the controller 205. In an aspect, the monitoring device 220 can be in communication with at least one sensor 225 that can gather signals to be converted into physiological data. For example, the monitoring device 220 can be an electrocardiogram (ECG) capture device, a blood pressure monitor, a heart rate monitor, a thermometer, an accelerometer, oxygen saturation monitor, bioimpedance stroke volume/cardiac output monitor, respiratory rate monitor, patient-activated symptom monitor, combinations thereof, and the like. In an aspect, the monitoring device 220 can be configured to retrieve physiological data such as, but not limited to, an oxygen saturation, a stroke volume, a cardiac output, a respiratory rate, a heart rate, a blood pressure, an atrioventricular contraction ratio, an interventricular activation pattern, presence of arrhythmias, combinations thereof, and the like.

In an aspect, the pacing device 105 can be used for cardiovascular conditioning. In an aspect, a user of the pacing device 105 can have the at least one electrode 125 disposed in or near the user's heart. In an aspect, the controller 205 can receive pulsing instructions 250 from a computing device via the communication element 210. The pulsing instructions 250 can comprise programmable instructions for a first series of electrical signals to be delivered to the heart of the user of the pacing device 105. In an aspect, the pulsing instructions 250 can comprise a rate at which the heart rate is going to increase, a target heart rate and a target duration to maintain the target heart rate, a time period to perform the first series of electrical signals, at least one physiological threshold, how to adjust the first series of electrical signals if the at least one physiological threshold is met, combinations thereof, and the like.

The controller 205 can process the pulsing instructions 250 and signal the pulse generator 215 to deliver the first series of electrical signals to the heart (e.g. right atrium). Initiation of the pulsing instructions can be triggered automatically by a timer or on-demand by the user of the device. The first series of electrical signals can be configured to increase a first heart rate, such as a resting heart rate, toward a target heart rate. As an example, the target heart rate can be 70-90% of the user's maximum predicted heart rate, which can be determined based on age (for example 220-age beats/minute) and/or condition. As an example, the first series of electrical signals can increase the first heart rate 5-10 beats per minute (bpm) every 0.5-5 minutes continuously or in steps. In an aspect, the monitoring device 220 can be receiving signals from the at least one sensor 225 and compiling the signals into physiological data that is communicated to the controller 205. The controller 205 can compare the physiological data to physiological parameters to determine whether any physiological thresholds have been met. For example, in an aspect, the controller 205 can determine whether at least one of a stroke volume threshold (5-10% below baseline), a cardiac output threshold (5% below baseline), a systolic blood pressure threshold (5-15 mmHg below baseline), an oxygen saturation threshold (92-94% oxygen saturation percentage or 3-5% from baseline oxygen saturation values), an arrhythmia threshold (any arrhythmia >3 beats or >1 second), a dyssynchrony threshold that indicates a loss of 1:1 or other optimal atrio-ventricular conduction/atrio-ventricular synchrony, a interventricular electrical activation pattern threshold (<90% baseline template match or QRS duration >110 msec), combinations thereof and the like has been met.

In an aspect, if at least one of the physiological thresholds have been met, the controller 205 can modify the first series of electrical signals to a second series of electrical signals that restores the at least one of the physiological thresholds to a desired level. For example, the controller 205 can cause the pulse generator 215 to deliver the second series of electrical signals to decrease the paced heart rate by 5-20 bpm immediately, and again every 2-30 sec until the physiological threshold level has been resolved or the user has returned to the first heart rate which can be the user's resting heart rate.

In an aspect, if none of the physiological thresholds have been met, then the controller 205 can cause the pacing device 105 to continue to deliver the first series of electrical signals to the user's heart until the target heart rate has been reached. When the target heart rate has been reached, the controller 205 can maintain the target heart rate with the first series of electrical signals for a target time period, for example 15-60 minutes, including, for example and without limitation, 15 minutes, 20 minutes, 25 minutes, 30 minutes, 35 minutes, 40 minutes, 45 minutes, 50 minutes, 55 minutes, or 60 minutes. Although exemplary target time periods are disclosed, it is contemplated that any desired time period can be used, including those falling above or below the exemplary range of 15-60 minutes. In exemplary aspects, it is contemplated that the target time period can be adjusted over time as cardiovascular conditioning occurs, reflecting an increase in the time a patient spends exercising as the patient progresses in a training program. The monitoring device 220 and the controller 205 can continue monitoring the user and determine whether a physiological threshold has been met, respectively, during the time period. In an aspect, the first series of electrical signals can be stopped after the time period or the first series of electrical signals can comprise electrical signals that ramp down the heart rate of the user until the resting or baseline heart rate is restored.

In an aspect, a pulsing protocol comprising the first series of electrical signals can be delivered to the user at different intervals (e.g., several times daily, once daily, every other day, and the like, for days, weeks, or longer, including indefinitely). The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning). In an aspect, the controller 205 and/or computer system in communication with the controller 205 can calculate a new pulsing protocol for each interval. The new pulsing protocol can be calculated based on the results of previous pulsing protocols, physiological data gathered from the user, physiological data and pulsing protocols of other users, combinations thereof, and the like.

Figure 3:
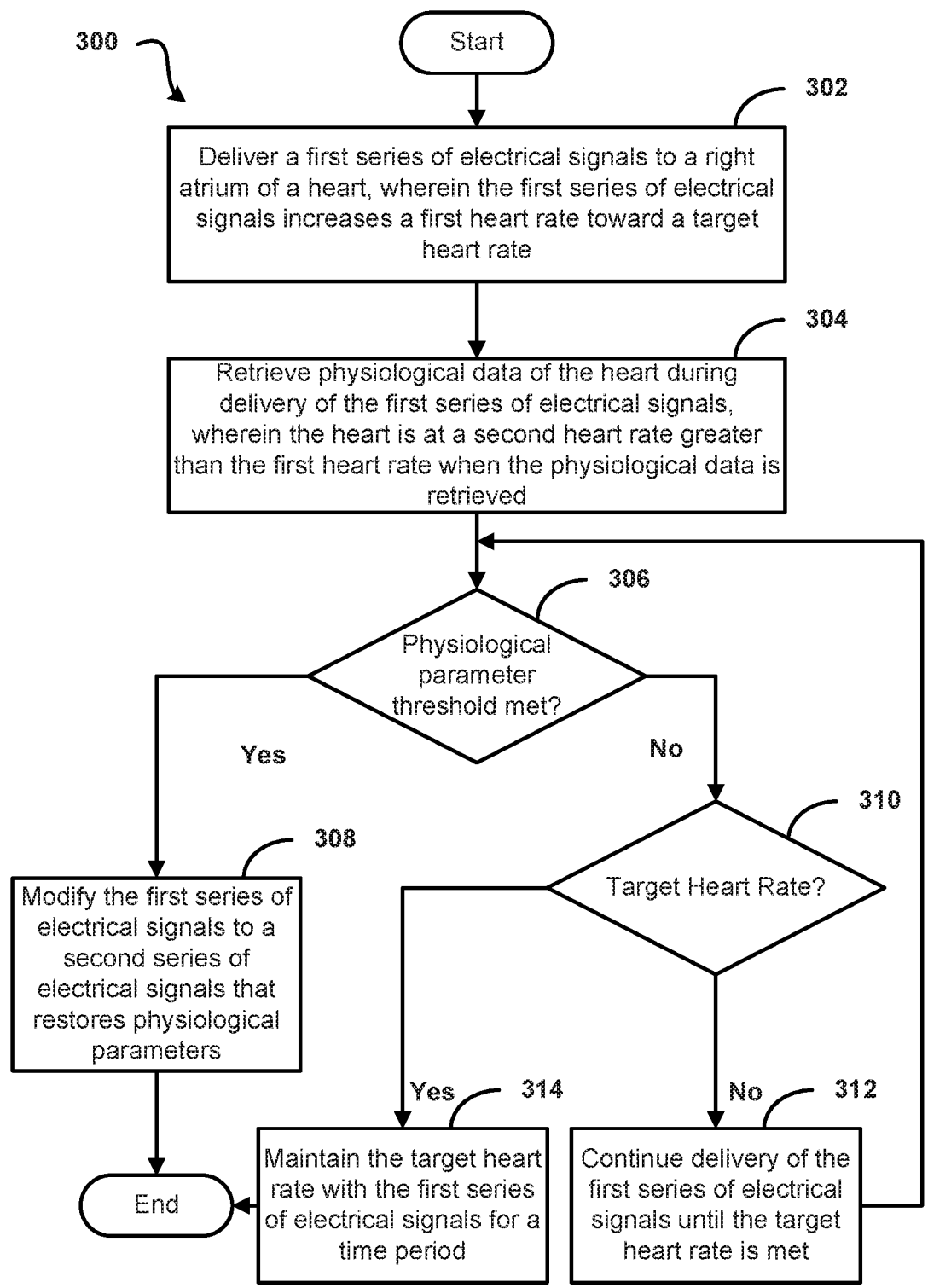
FIG. 3 is a flowchart of an example method.

FIG. 3 illustrates a method 300 for cardiovascular conditioning. In step 302, a pacing device, such as pacing device 105, can deliver a first series of electrical signals to a right atrium of a heart of a user. The first series of electrical signals can increase a first heart rate of the heart toward a target heart rate. In an aspect, the first heart rate can be a resting heart rate of the user. In an aspect, a determination can be made as to what the target heart rate should be. In an aspect, the determination of the target heart rate can be based on age or other physiological parameters. In an aspect, the pacing device can deliver the electrical signals to an electrode implanted in the myocardium of the right atrium of the heart of the user. In an aspect, the first series of electrical signals can be predetermined and sent to the pacing device by a computing device. The first series of electrical signals can comprise acceleration electrical signals that increase the heart rate of the heart and holding electrical signals that maintain the heart rate once the heart rate has reached the target heart rate.

In step 304, a monitoring device can determine physiological data of the user during the delivery of the first series of electrical signals. In an aspect, the monitoring device can be in communication with at least one sensor that detects a physiological characteristic of the heart and/or user. In an aspect, the monitoring device 220 can be receiving signals from the at least one sensor 225 and compiling the signals into physiological data that is communicated to the controller 205. The controller 205 can compare the physiological data to physiological parameters to determine whether any physiological thresholds have been met. For example, in an aspect, the controller 205 can determine whether at least one of a stroke volume threshold, a cardiac output threshold, a systolic blood pressure threshold, an oxygen saturation threshold, an arrhythmia threshold, a dyssynchrony threshold that indicates a loss of 1:1 or other optimal atrio-ventricular conduction/atrio-ventricular synchrony, a inter-ventricular electrical activation pattern threshold, a patient-activated symptom threshold, combinations thereof and the like has been met.

In step 306, the controller 205 can determine whether at least one of the physiological parameters has met a physiological threshold based on the physiological data. For example, the controller 205 can determine whether an atrio-ventricular synchrony has met a dyssynchrony threshold that indicates atrio-ventricular dyssynchrony based on the physiological data.

In step 308, if the controller 205 determines at least one of the physiological parameters has met the physiological threshold, then the controller 205 can modify the first series of electrical signals to a second series of electrical signals that can restore the at least one physiological parameter back to acceptable levels. For example, the controller 205 can signal the pulse generator 210 to deliver a second series of electrical signals that can lower the current paced heart rate to a lower heart rate until the physiological parameter is at an acceptable level. The controller 205 can then signal the pulse generator 210 to deliver electrical signals to maintain the lower heart rate that results in the physiological parameters being at acceptable levels. The lower heart rate can be higher than the resting heart rate of the user.

In step 310, if the controller 205 determines that the at least one of the physiological parameters has not met a physiological threshold, then the controller 205 can determine, in step 312, whether the target heart rate has been met. If the target heart rate has not been met, the controller 205 can continue to signal the pulse generator 215 to deliver the first series of electrical signals to the heart. The method 300 can then proceed back to step 306. In step 310, if the target heart rate has been reached then the method can proceed to step 314. In step 314, the controller 205 can signal the pulse generator 215 to maintain the target heart rate for a target time period. In an aspect, the method can end once this time period target has been met. In an another aspect, the controller 205 can signal the pulse generator 215 to decrease the heart rate until the first heart rate is reached. Performing the methods herein repeatedly at various intervals can improve heart failure symptoms and outcomes, reduce heart injury during surgery, coronary angioplasty/stenting or other intervention stressful to the heart, improve exercise tolerance, reduce angina pain in people with heart disease, combinations thereof, and the like.

Figure 4:
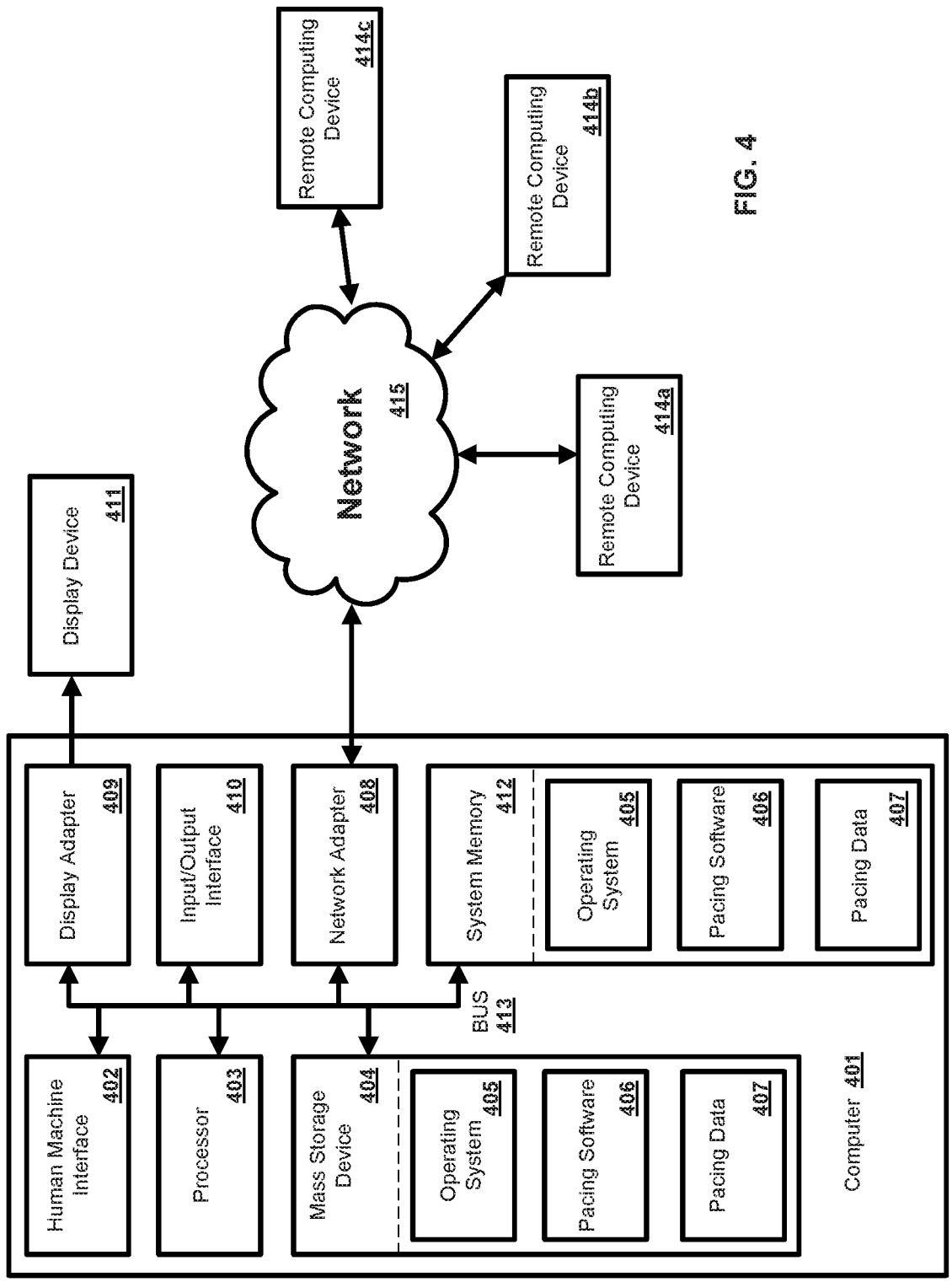
FIG. 4 is block diagram illustrating an example computing system in which the disclosed methods and systems can operate.

The system has been described above as comprised of units. One skilled in the art will appreciate that this is a functional description and that the respective functions can be performed by software, hardware, or a combination of software and hardware. A unit can be software, hardware, or a combination of software and hardware. In one exemplary aspect, the units can comprise a computer 401 as illustrated in FIG. 4 and described below. As an example, the computer 401 can be the pacing device 105 and/or the controller 205 of the pacing device.

FIG. 4 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 401. The components of the computer 401 can comprise, but are not limited to, one or more processors or processing units 403, a system memory 412, and a system bus 413 that couples various system components including the processor 403 to the system memory 412. In the case of multiple processing units 403, the system can utilize parallel computing.

The system bus 413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 413, and all buses specified in this description can also be implemented over a wired or wireless network connection and each of the subsystems, including the processor 403, a mass storage device 404, an operating system 405, pacing software 406, pacing data 407, a network adapter 408, system memory 412, an Input/Output Interface 410, a display adapter 409, a display device 411, and a human machine interface 402, can be contained within one or more remote computing devices 414*a,b,c* at physically separate locations, connected through buses of this form, in effect implementing a fully distributed system.

The computer 401 can comprise a variety of computer readable media. Exemplary readable media can be any available media that is accessible by the computer 401 and comprises, for example and not meant to be limiting, both volatile and non-volatile media, removable and non-removable media. The system memory 412 comprises computer readable media in the form of volatile memory, such as random access memory (RAM), and/or non-volatile memory, such as read only memory (ROM). The system memory 412 can contain data such as pacing data 407 and/or program modules such as operating system 405 and pacing software 406 that are immediately accessible to and/or are presently operated on by the processing unit 403.

In another aspect, the computer 401 can also comprise other removable/non-removable, volatile/non-volatile computer storage media. By way of example, FIG. 4 illustrates a mass storage device 404 which can provide non-volatile storage of computer code, computer readable instructions, data structures, program modules, and other data for the computer 401. For example and not meant to be limiting, a mass storage device 404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 404, including by way of example, an operating system 405 and pacing software 406. Each of the operating system 405 and pacing software 406 (or some combination thereof) can comprise elements of the programming and the pacing software 406. Pacing data 407 can also be stored on the mass storage device 404. Pacing data 407 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 401 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 403 via a human machine interface 402 that is coupled to the system bus 413, but can be connected by other interface and bus structures, such as a parallel port, game port, an IEEE 1394 Port (also known as a Firewire port), a serial port, or a universal serial bus (USB).

In yet another aspect, a display device 411 can also be connected to the system bus 413 via an interface, such as a display adapter 409. It is contemplated that the computer 401 can have more than one display adapter 409 and the computer 401 can have more than one display device 411. For example, a display device can be a monitor, an LCD (Liquid Crystal Display), or a projector. In addition to the display device 411, other output peripheral devices can comprise components such as speakers (not shown) and a printer (not shown) which can be connected to the computer 401 via Input/Output Interface 410. Any step and/or result of the methods can be output in any form to an output device. Such output can be any form of visual representation, including, but not limited to, textual, graphical, animation, audio, tactile, and the like.

The computer 401 can operate in a networked environment using logical connections to one or more remote computing devices 414*a,b,c*. By way of example, a remote computing device can be a personal computer, portable computer, a server, a router, a network computer, a peer device or other common network node, and so on. Logical connections between the computer 401 and a remote computing device 414*a,b,c* can be made via a local area network (LAN) and a general wide area network (WAN). Such network connections can be through a network adapter 408. A network adapter 408 can be implemented in both wired and wireless environments. Such networking environments are conventional and commonplace in offices, enterprise-wide computer networks, intranets, and the Internet 415.

For purposes of illustration, application programs and other executable program components such as the operating system 405 are illustrated herein as discrete blocks, although it is recognized that such programs and components reside at various times in different storage components of the computing device 401, and are executed by the data processor(s) of the computer. An implementation of pacing software 406 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

EXPERIMENTAL EXAMPLES

The presently described technology and its advantages will be better understood by reference to the following examples. These examples are provided to describe non-exhaustive embodiments of the present technology. By providing these examples, the scope of the presently described and claimed technology is not limited in spirit or scope. It will be understood by those skilled in the art that the full scope of the presently described technology encompasses at least the subject matter defined by the claims appending this specification, and any alterations, modifications, derivatives, combinations, or equivalents of those claims. Further, the citations provided herein are hereby incorporated by reference for the cited subject matter Example 1

Normal function of cardiac ATP-sensitive potassium ("$K_{ATP}$") channels has been linked with tolerance of an array of physiologic or pathologic stresses. While the therapeutic use of cardiac $K_{ATP}$ channel opening drugs can be problematic due to undesired systemic effects, the physiologic function of these sarcolemmal $K_{ATP}$ channels can be targeted by manipulating their transcription and translation or their trafficking in tissue-specific ways. Further, exercise can result in basal upregulation of functional $K_{ATP}$ channels on the membrane of heart cells from the ventricles, resulting in greater adaptation of action potential duration to sustained heart rate ("HR") increases even within the normal physiologic range for daily activities including exercise, and thus reduced myocardial $O_2$ consumption. Resistance to injury from myocardial ischemia can have a significant dependence on baseline $K_{ATP}$ channel expression, accounting for a major part of the beneficial effect of exercise on infarct size.

Animal Data

In one experimental example, a custom bipolar pacing catheter was inserted into the esophagus of sedated mice positioned supine on a warmed pad, as shown in FIG. 5. Pacing was delivered by selectively capturing the atria as monitored by an ECG and, over 15 minutes, gradually increasing the HR by pacing from the resting HR (~400 bpm or 150 msec coupling interval, CI) to the maximum HR achievable while maintaining 1:1 atrioventricular ("AV") synchrony without aberrancy (~750 bpm, 80 msec CI), which reflects the maximum HR during treadmill exercise observed in mice with implanted hemodynamic monitors, assessed by continuous surface ECG (shown in FIGS. 6A and 6B). Feedback of the physiologic parameter to the paced rate was achieved by visual inspection of the surface electrograms for A:V and V:V synchrony with manual downward adjustment of the paced HR if the desired synchronous relationship was not observed to be maintained at a particular HR. Once the targeted HR or a maximal HR that allowed for 1:1 A:V relationship and no evidence of ventricular dyssynchrony was reached, the HR was maintained for 45 minutes or was adjusted downward in 25 bpm increments as needed over 45 minutes to maintain 1:1 A:V synchrony and to avoid aberrancy as determined by visual observation of the surface ECG. After these 45 minutes of sustained high HR, the paced HR was then gradually reduced over the next 15 minutes until the intrinsic HR was restored or until the paced HR was below the intrinsic HR. Because pacing was bipolar with the current set just above atrial capture threshold, no skeletal muscle or diaphragmatic capture occurred. Sham-paced mice underwent sedation and placement of the pacing catheter and were otherwise treated identically to pacing intervention-treated mice but with no actual pacing. Pacing intervention or sham treatment was repeated once daily, 5 days per week, for a total of 7 treatment days. One day after the final episode of pacing vs. sham, either the left ventricle ("LV") was freeze clamped, or the entire heart was isolated and retrogradely perfused for cell isolation, measurement of $O_2$ consumption as a function of paced HR, or ischemic preconditioning/ischemia reperfusion ("IP/IR") protocol.

$K_{ATP}$ Channel Expression

Figure 7A:
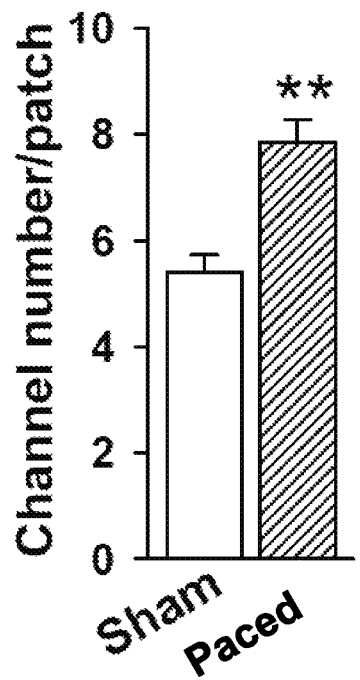
FIG. 7A shows $K_{ATP}$ channels per patch in isolated ventricular myocytes from paced (n=71 cells, 5 mice) vs. sham (n=40 cells, 4 mice) mice. The p-value (**) is less than 0.01.
Figure 7B:
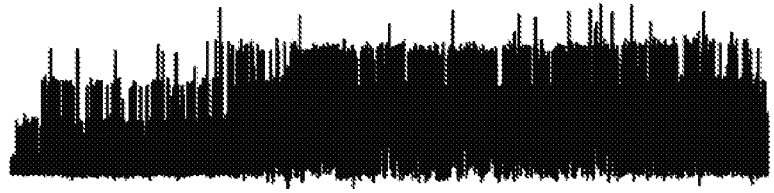
FIG. 7B shows a representative single channel tracing from sham mice.
Figure 7C:
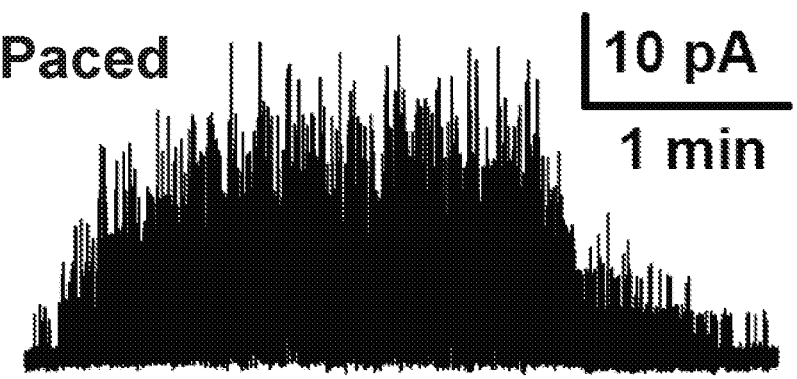
FIG. 7C shows a representative single channel tracing from paced mice.

In ventricular myocytes isolated from hearts of mice, the pacing intervention was associated with more cardioprotective ATP-sensitive potassium ("$K_{ATP}$") channels per patch (7.8 mean±0.44 S.E. vs. 5.4±0.33 for sham, p<0.01, FIGS. 7A-7C) measured. The sham and pacing-induced $K_{ATP}$ channel surface densities were comparable to previously identified sedentary and exercise levels, respectively. Normal $K_{ATP}$ channel properties are linked with tolerance of an array of physiologic or pathologic stresses. In response to exercise, basal upregulation of functional $K_{ATP}$ channels on the membrane of heart cells from the ventricles of mice can result in greater adaptation of ventricular action potential duration to acute HR increases and thus reduced myocardial $O_2$ consumption. Resistance to injury from myocardial ischemia can also have a significant dependence on $K_{ATP}$ channel expression, accounting for a major part of the beneficial effect of exercise on infarct size.

IP/IR

Figure 8:
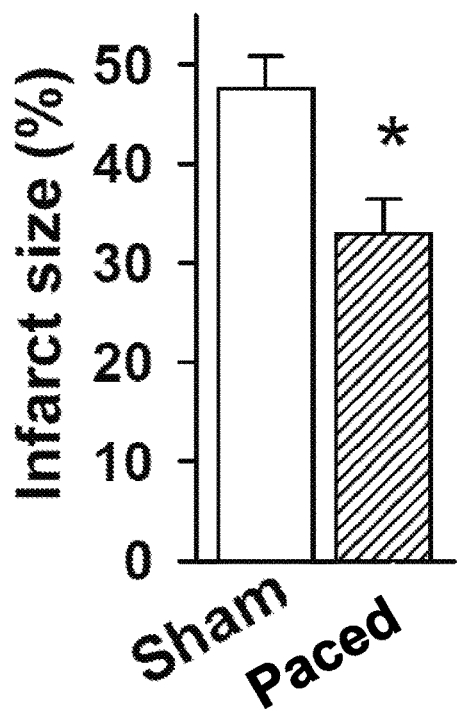
FIG. 8 is a graph showing summary statistics of infarct size as percentage of total area of ventricles from paced vs. sham treated mice (n=4). The p-value (*) is less than 0.05.

Augmented stress-resistance, reflected by smaller infarct sizes, occurs in response to IP/IR of isolated hearts from the paced vs. sham treated mice (infarcted area as a percentage of area at risk 32.96±3.47 vs. 47.62±3.2% for sham, p<0.05, FIG. 8), a response previously linked to $K_{ATP}$ channel function. Specifically, for IP/IR, two 2 minute cycles of global ischemia (stop flow) were delivered to heart isolated from the paced vs. sham treated mice, followed by 5 minutes of reperfusion each, and then 20 minutes of global ischemia and 45 minutes of reperfusion. Hearts were then immediately frozen at −20° C., cut transversely every ~0.8 mm, and incubated in 1% triphenyltetrazolium chloride (TTC) in phosphate buffer at 37° C. After staining, sections were fixed in formaldehyde. Areas of MI were determined in images of gross sections by ImageJ software.

OPA1 Expression and Apoptosis

Figure 9:
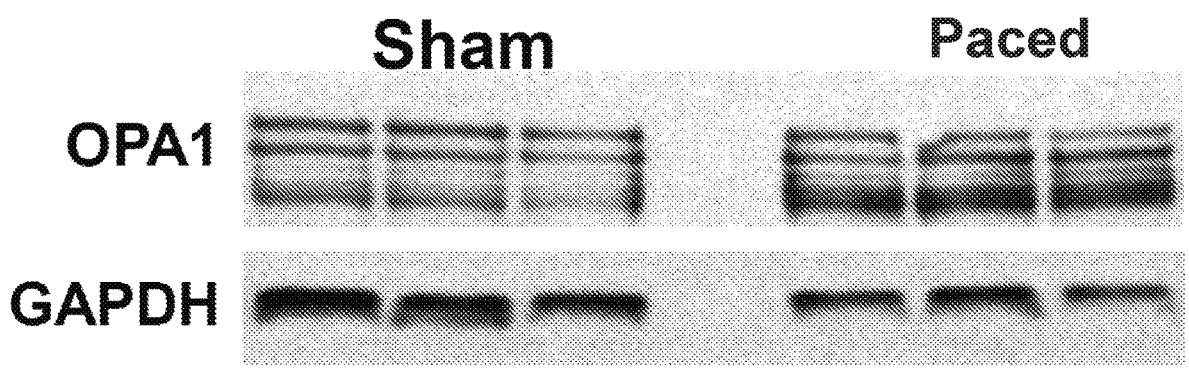
FIG. 9 shows exemplary OPA1 expression by immuno-electrophoresis of a whole cell protein extracted from the left ventricles of paced and sham treated mice (n=3 each).
Figure 10A:
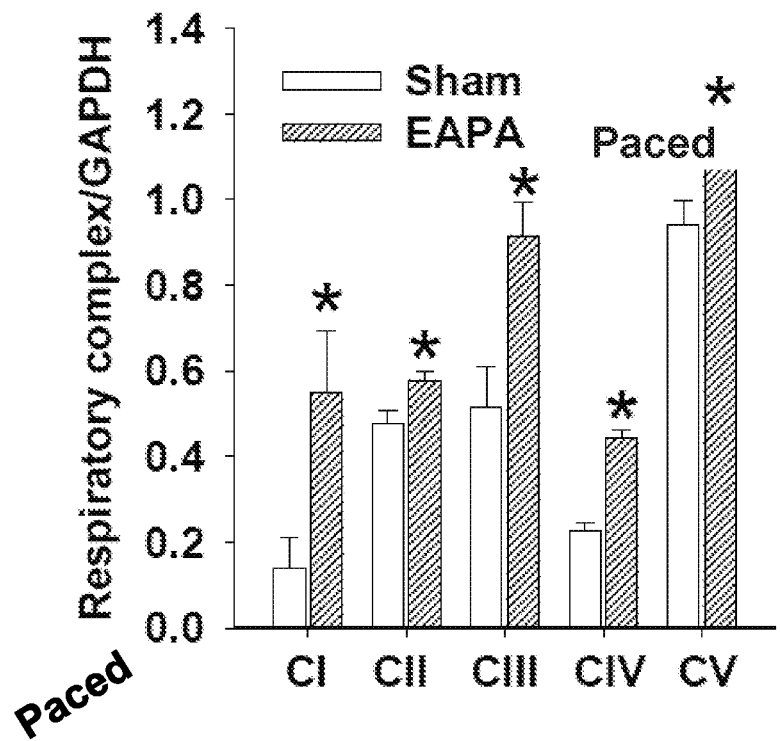
FIG. 10A is a graph showing respiratory complex expression normalized to GAPDH from ventricles of paced vs. sham treated mice (n=4 each). The p-value (*) is less than 0.05.
Figure 10B:
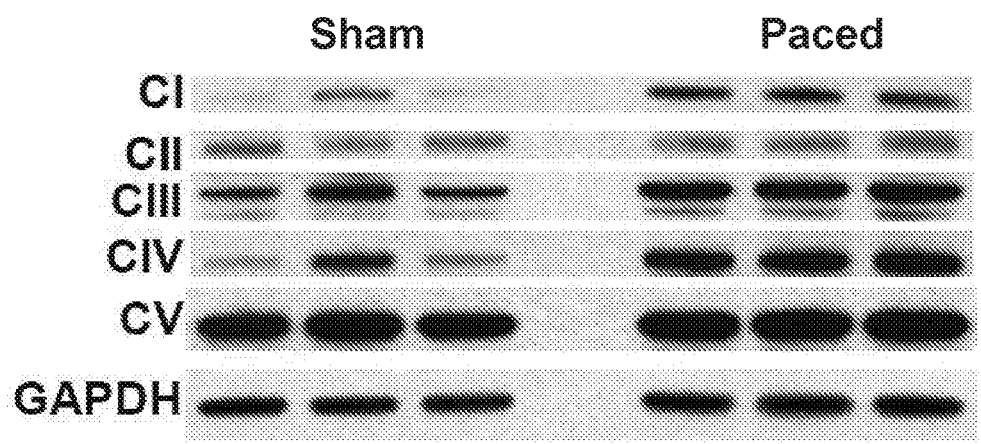
FIG. 10B shows respiratory complex expression normalized to GAPDH from ventricles of paced vs. sham treated mice.

The pacing vs. sham intervention in mice is coupled with an ~3-fold increased LV expression of OPA1 normalized to glyceraldehyde-3-phoshate dehydrogenase ("GAPDH") (1.41±0.06 vs. 0.54±0.22 AU for sham, p<0.05, FIG. 9), and a subset of mitochondrial respiratory complex components normalized to GAPDH (0.55±0.15 vs. 0.14±0.07 AU for CI, 0.58±0.02 vs. 0.48±0.03 AU for CII, 0.92±0.08 vs. 0.52±0.09 AU for CIII, 0.44±0.02 vs. 0.23±0.02 AU for CIV and 1.14±0.06 vs. 0.94±0.06 for CV, all p<0.05, FIGS. 10A and 10B).

Starting on the day of completion of the pacing vs. sham intervention protocol, groups of mice underwent 2 daily injections of isoproterenol 10 mg/kg i.p. followed 24 hours later by TUNEL staining of sections of the left ventricles for apoptosis. The pacing intervention was associated with significantly fewer apoptotic nuclei (6.68±1.03% of all nuclei, n=3 hearts) compared to sham (14.89±1.78%, n=3 hearts, p<0.01).

Exercise-induced modification of mitochondrial function and structure is a well-recognized basis for beneficial cardiovascular conditioning. Mitochondria represent approximately one-third of the cardiac mass and play a critical role in maintaining cellular function; however, mitochondria are also a potent source of toxic reactive oxygen species ("ROS") and pro-apoptotic factors. As such, maintaining mitochondrial homeostasis is essential to cell health and survival. OPA1 is a dynamin-related large GTPase located on the inner membrane of mitochondria at the narrow junctions between cristae and the boundary membrane. OPA1 can be a regulator of mitochondrial fusion. In addition, OPA1 can play a role in mitochondria DNA stabilization, enhanced expression of respiratory protein complexes and regulation of stress-induced cristae remodeling. Overall, OPA1 can function to increase mitochondrial respiratory efficiency, blunt release of pro-apoptotic cytochrome C and limit generation of ROS. Reduced cardiac OPA1 expression can be linked to susceptibility to ischemic injury and HF in humans and animal models. Exercise can upregulate cardiac OPA1, and its mild transgenic overexpression can protect mice from MI due to IR.

Combined cardiac knock out of proliferator-activated receptor coactivator (PGC)-1α and β reduces OPA1 levels. Indeed PGC1α, also upregulated by exercise, can be a master regulator of mitochondrial biogenesis in both skeletal and cardiac muscle, particularly via regulation of genes encoding proteins involved in oxidative phosphorylation. Hearts lacking PGC1α can not generate sufficient ATP for increased work output and develop mechanical dysfunction over time.

Post-Infarct Remodeling

Fourteen days after ligation of the left-anterior descending artery, mice were exposed 5 days per week to 4 weeks of the pacing vs. sham intervention. The area of fibrosis in serial sections of the left ventricles stained with trichrome was quantified by Image J software (n=3 each). This analysis shows a trend toward less fibrosis in paced hearts (17.7±1.5% for paced vs. 50±8.7% for sham, n=3 hearts each, p=0.1). In separate hearts, sections of left ventricles remote from the scar were assessed for apoptosis by TUNEL staining. The pacing intervention results in significantly less post-infarct apoptosis compared with sham treatment ((9.4±4.2% of nuclei vs. 37.1±4.7% for sham, n=3 hearts each, p<0.05 for each assay).

In summary, the pacing intervention results in upregulation of cardioprotective and metabolic pathways in the left ventricles of the hearts of animals associated with improved myocardial stress tolerance, reduced injury, reduced apoptosis, and reduced fibrosis.

Human Data

Heart rate acceleration can be well-tolerated, even in people with severe cardiac disease such as heart failure (HF). This is demonstrated in such patient populations by maintained hemodynamics with sustained HR acceleration as delivered during invasive cardiac electrophysiology studies and by their tolerance of cardiac rehabilitation programs. The following tests are illustrative of a clinical application of the pacing intervention disclosed herein and its safety and tolerability among those with severe cardiovascular disease.

Single Pacing Episodes

Figure 11A:
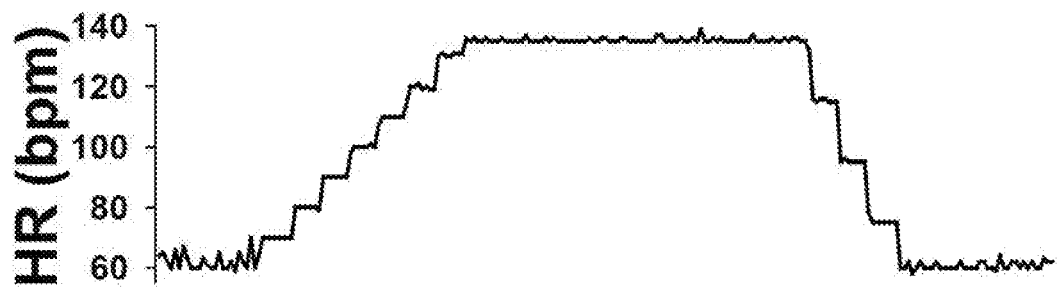
FIG. 11 shows representative tracings during pacing intervention of HR (FIG. 11A), cardiac output (CO, FIG. 11B), and total peripheral resistance (TPR, FIG. 11C) profiles in a human subject as measured by impedance cardiography.
Figure 11B:
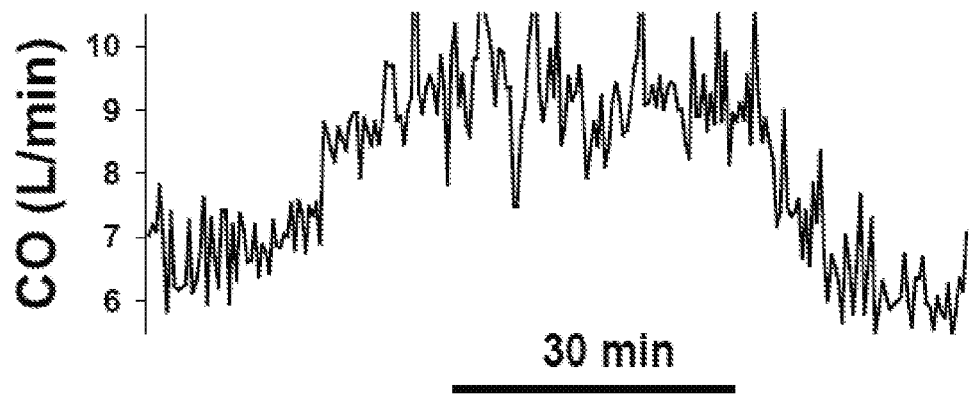
Figure 11C:
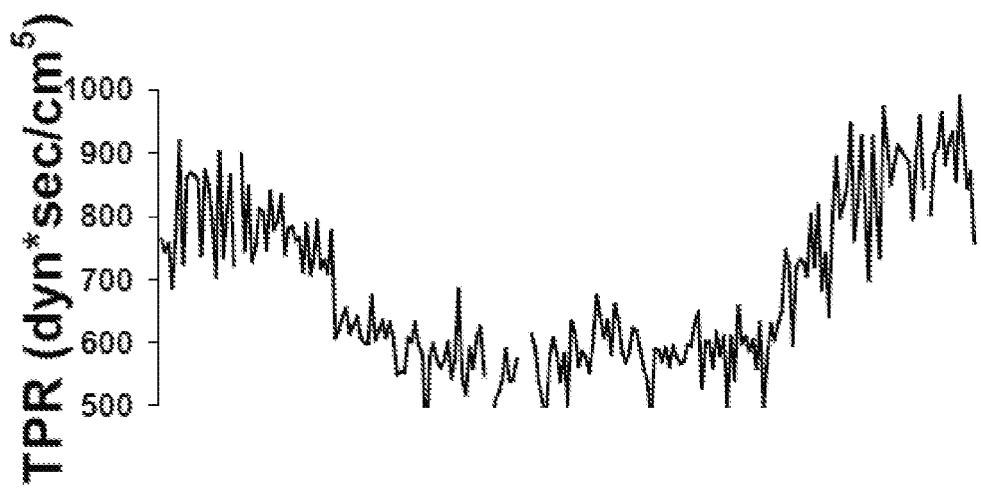

Four patients with stable, medically-refractory non-ischemic cardiomyopathy, left ventricular ejection fraction ("EF") <35%, and chronically implanted cardioverter defibrillators ("ICDs" or "BiV/ICDs") with atrial leads, without atrial fibrillation or any limiting valve, lung or other systemic illness, underwent single episodes of the pacing intervention. The subjects were 3 males and one female, three of whom were Caucasian and one African American. Two had ICDs with biventricular pacing and two had standard ICDs. The average (±S.D) characteristics of the 4 subjects are: age 59±7 years, EF 25±6%, 6-min walk distance 1567±368 feet, serum creatinine 1.3±0.4 mg/dL, NT-proBNP 526±244 pg/mL, Minnesota Living with Heart Failure questionnaire (MLHF) score 42±34, QRS duration (intrinsic for those with ICDs or BiV paced for those with BiV/ICDs) 115±4 msec. All were considered to have clinically severe cardiovascular disease. With the subjects reclined and with an empty stomach, the pacing intervention was delivered by manual reprogramming of their implanted pacing device to accelerate HR by 10 bpm every 2.5 minutes from their resting rate to a target heart rate of 80% of maximum predicted heart rate (80% MPHR=0.8*[220−age]) with downward adjustment of this goal based on visual inspection of intracardiac and surface electrograms as well as other objective and subjective feedback criteria, as described herein. Subjects with dual chamber ICDs were paced only in the atrium. Subjects with BiV/ICDs underwent sequential atrial and biventricular pacing to maintain A:V and V:V synchrony. The maximum achieved rate was maintained for 30 minutes as long as 1:1 atrio-ventricular synchrony, QRS duration and morphology, vital sign, and symptom feedback criteria were met, then reduction by 20 bpm every 2.5 minutes until the baseline HR was restored (FIG. 11A). The vital sign and symptom feedback criteria included the combination of a 10 mmHg or greater decrease in systolic blood pressure ("SBP") from baseline, 5% or greater decrease in $SaO_2$ from baseline, a 5% or greater decrease in cardiac output ("CO") from baseline (for those subjects in whom this parameter was measured), ventricular or atrial runs of 3 or more ectopic beats, or any uncomfortable symptoms, including chest pain, shortness of breath or palpitations. Three subjects also had CO and total peripheral resistance ("TPR") measured by bioimpedance (FIG. 11B and FIG. 11C, respectively) and any drop in CO during HR acceleration was used as a feedback criterion, along with the others listed, to adjust HR downward in these subjects. Subjects were observed for 30 minutes after the protocol was complete and HR was restored back to resting level in order to assess for any late changes in symptoms, vital signs or arrhythmias.

All subjects achieved 80% MPHR and all but one were able to maintain that rate for the full 30 minutes. One subject had a decrease in SBP after 15 minutes at 80% MPHR (130 bpm) triggering deceleration of pacing from 80% MPHR to 75% MPHR (125 bpm) for 5 min and then 70% (115 bpm) for 10 minutes in order to maintain the blood pressure within the predetermined limits. The rate was returned to baseline at the end of 30 min total acceleration. One-to-one AV synchrony and stable ventricular activation pattern and QRS duration were maintained throughout in all subjects. There were no limiting symptoms of chest pressure, shortness of breath, lightheadedness, palpitations or any other discomfort in any subject during the pacing intervention. Vital signs for the group of subjects, other than HR, were not significantly different at 30 minutes of maximum paced HR than at baseline: SBP 104±15 vs. 100±7 mmHg, diastolic BP 72±11 vs. 69±8 mmHg, $O_2$ saturation ($SaO_2$) 97±3 vs. 97±2%, and respiratory rate (RR): 18±2 vs. 17±3, all n=NS. However, at 30 minutes of maximum paced HR vs. baseline there was significantly increased CO (9.4±0.9 vs. 5.6±1.4 L/min, p<0.05) and decreased TPR (647±50 vs. 917±104 dyn*s/$cm^5$, p<0.05). There were no differences in these parameters at the end of the pacing intervention vs. at baseline (5.4±1.1 L/min and 977±125 dyn*s/$cm^5$, respectively, both n=NS) nor were there significant differences in vital signs at these points. There were no arrhythmias other than isolated premature ventricular contractions in any subject. These data illustrate implementation of a form of the pacing approach described herein using manual adjustment of a pacing device to feedback physiologic parameters on the paced rate. The data also illustrate the hemodynamic and symptomatic tolerability of the pacing in subjects with severe cardiovascular disease. The effect on TPR indicates a beneficial extracardiac effect of the pacing intervention.

Repeated Pacing Treatments

A 67 year old Caucasian man with long-standing non-ischemic cardiomyopathy, EF 24% and New York Heart Association class IIIA, stage C-D HF despite chronic optimal medical management, MLHF score 49, $VO_2$ 13.7 ml/kg/min with peak METS of 3.91 on cardiopulmonary stress testing and 1415 feet on 6-min walk, a BiV paced QRS duration of 120 msec, underwent delivery of the pacing intervention 3-5 days per week for 4 weeks for a total of 15 sessions, via manual programming of his already-implanted BiV/ICD. The pacing intervention protocol was identical to that delivered for single episodes as described herein.

The 80% MPHR goal was achieved at every session and maintained for a full 30 minutes each session (no limiting criteria were met). On average (±S.D.), vital signs other than HR were not significantly different at 30 minutes of maximum paced rate than at baseline, except for $SaO_2$ and RR: (SBP 97±9 vs. 96±4 mmHg, p=NS, DBP 70±7 vs. 67±7 mmHg, p=NS, MAP 76±7 vs. 73±6 mmHg, p=NS, $SaO_2$ 95±1 vs. 97±1%, p<0.05, RR 17±2 vs. 16±2 breaths/min, p=0.04, at peak paced rate vs. baseline, respectively). There were no significant differences in any of these vital signs at the end of the pacing intervention vs. at baseline. There were no arrhythmias other than isolated premature ventricular contractions which were present at baseline. There were no bothersome symptoms of chest pressure, shortness of breath, lightheadedness, palpitations or any other discomfort during the pacing intervention. One-to-one AV synchrony and a stable ventricular activation pattern and QRS duration were maintained throughout. There were no heart failure exacerbations, arrhythmias or changes in medications during the 4 weeks of testing. Clinical tests immediately after the 4 weeks of pacing intervention, compared with baseline, are as follows: weight 187.6 vs. 187.7 lbs, serum creatinine 1.5 vs. 1.7 mg/dL, NT-pro-BNP 852 vs. 798 pg/mL, MLHF score 38 vs. 49, 6-minute walk distance 1358 vs. 1415 feet, 6-minute walk METS 2.96 vs. 3.05, cardiopulmonary stress test $VO_2$ 14.1 vs. 13.7 ml/kg/min and METS 4.02 vs. 3.91, EF by echocardiography 20% vs. 24%, and biventricular pacing 99% vs. 97%. The subject underwent previously planned surgical placement of a left ventricular assist device 8 weeks after completion of the pacing intervention and was also listed for a heart transplant. Only some of the clinical tests improved while others remained stable for this individual. However, given the general progressive decompensation of patients with severe heart disease, stability in some markers can represent an overall beneficial outcome. In summary, these data do indicate that the pacing intervention is hemodynamically and symptomatically well-tolerated in a target population.

EXEMPLARY ASPECTS

In view of the described systems and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1

A method comprising: delivering a first series of electrical signals to a heart of a user, wherein the first series of electrical signals increases a first heart rate of the heart toward a target heart rate; retrieving physiological data of the user during delivery of the first series of electrical signals, wherein the heart is at a second heart rate greater than the first heart rate when the physiological data is retrieved; determining whether a physiological parameter has met a physiological threshold based on the physiological data; if the physiological threshold has been met, modifying the first series of electrical signals to a second series of electrical signals that restores the physiological parameter to an acceptable level; and if the physiological threshold has not been met, continuing delivery of the first series of electrical signals until the target heart rate is met for a target time duration.

Aspect 2

The method of aspect 1, further comprising, maintaining the target heart rate with the first series of electrical signals for a time period.

Aspect 3

The method of any one of the preceding aspects, wherein the first series of electrical signals are configured to induce favorable myocardial remodeling of the heart.

Aspect 4

The method of any one of the preceding aspects, wherein the second series of electrical signals that restores the physiological parameter decreases the second heart rate to a third heart rate.

Aspect 5

The method of aspect 5, further comprising, maintaining the third heart rate with the second series of electrical signals for a time period.

Aspect 6

The method of any one of the preceding aspects, wherein the second series of electrical signals are configured to induce favorable myocardial remodeling of the heart.

Aspect 7

The method of any one of the preceding aspects, wherein the physiological parameter is optimal atrio-ventricular and interventricular synchrony and the physiological threshold is a dyssynchrony threshold.

Aspect 8

The method of any one of the preceding aspects, wherein determining whether a physiological parameter has met a physiological threshold comprises determining whether a plurality of physiological parameters have met a physiological threshold, and wherein the plurality of physiological parameters comprises optimal atrio-ventricular and interventricular synchrony and at least one other selected variable.

Aspect 9

The method of aspect 8, wherein the at least one other selected variable comprises blood pressure.

Aspect 10

The method of aspect 8, wherein the at least one other selected variable comprises respiratory rate.

Aspect 11

The method of aspect 8, wherein the at least one other selected variable comprises a bioimpedance measurement of stroke volume.

Aspect 12

A system comprising: a pulse generator configured to deliver a first series of electrical signals to a heart wherein the first series of electrical signals increases a first heart rate of the heart toward a target heart rate; a monitoring device configured to retrieve physiological data from a user of the system before and while the heart is receiving the first series of electrical signals; and a controller comprising: a memory comprising computer readable instructions, and a processor that, when executing the computer readable instructions, is configured to: determine whether a physiological parameter has met a physiological threshold based on the physiological data; if the physiological threshold has been met, modify the first series of electrical signals to a second series of electrical signals that restores the physiological parameter to an acceptable level; and if the physiological threshold has not been met, continue delivery of the first series of electrical signals until the target heart rate is met.

Aspect 13

The system of aspect 12, wherein the processor is configured to maintain the target heart rate with the first series of electrical signals for a time period.

Aspect 14

The system of any one of aspects 12-13, wherein the first series of electrical signals are configured to induce favorable myocardial remodeling of the heart.

Aspect 15

The system of any one of aspects 12-14, wherein the second series of electrical signals that restore the physiological parameter is configured to decrease the second heart rate to a third heart rate.

Aspect 16

The system of aspect 15, wherein the processor is configured to maintain the third heart rate with the second series of electrical signals for a time period.

Aspect 17

The system of any one of aspects 12-16, wherein the second series of electrical signals are configured to induce favorable myocardial remodeling of the heart.

Aspect 18

The system of any one of aspects 12-17, wherein the physiological parameter is optimal atrio-ventricular and interventricular synchrony and the physiological threshold is a dyssynchrony threshold.

Aspect 19

The system of any one of aspects 12-18, wherein the processor is configured to determine whether a plurality of physiological parameters have met a physiological threshold based on the physiological data, and wherein the plurality of physiological parameters comprises optimal atrio-ventricular and interventricular synchrony and at least one other selected variable.

Aspect 20

The system of aspect 19, wherein the at least one other selected variable comprises blood pressure.

Aspect 21

The system of aspect 19, wherein the at least one other selected variable comprises respiratory rate.

Aspect 22

The system of aspect 19, wherein the at least one other selected variable comprises a bioimpedance measurement of stroke volume.

Aspect 23

A method comprising: analyzing physiologic or symptomatic markers of hemodynamic and symptomatic stability of a heart; determining a target heart rate for the heart based upon the analysis of hemodynamic and symptomatic stability; delivering a series of electrical signals to the heart, wherein the series of electrical signals increases a heart rate of the heart above a resting heart rate to the target heart rate, and wherein the series of electrical signals ensure optimal atrio-ventricular and interventricular synchrony while increasing the heart rate to the target heart rate and maintaining the heart rate at the target heart rate for a target duration.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
   delivering a first series of electrical signals to an atrium of a heart of a user, wherein the first series of electrical signals increases a first heart rate of the heart toward a target heart rate;
   retrieving physiological data of the user during delivery of the first series of electrical signals, wherein the heart is at a second heart rate greater than the first heart rate when the physiological data is retrieved;
   determining whether at least two physiological parameters are each within a respective physiological threshold based on the physiological data, wherein the at least two physiological parameters comprise an optimal atrio-ventricular synchrony and an optimal interventricular synchrony, wherein the respective physiological threshold of the optimal atrio-ventricular synchrony comprises an atrio-ventricular dyssynchrony threshold, wherein the atrio-ventricular dyssynchrony threshold comprises an atrio-ventricular conduction ratio and an atrio-ventricular delay, and wherein the respective physiological threshold of the optimal interventricular synchrony comprises an interventricular dyssynchrony threshold;
   if at least one physiological parameter of the at least two physiological parameters is outside of the respective physiological threshold, modifying the first series of electrical signals to a second series of electrical signals that restores the at least one physiological parameter to an acceptable level; and
   if each of the at least two physiological parameters is within the respective physiological threshold, continuing delivery of the first series of electrical signals until the target heart rate is met for a target time duration.

2. The method of claim 1, wherein the atrio-ventricular conduction ratio has an upper limit of 1.2:1 and a lower limit of 0.8:1 and the atrio-ventricular delay has an atrio-ventricular interval upper limit of 200 msec and an atrio-ventricular interval lower limit of 120 msec.

3. The method of claim 1, wherein the interventricular dyssynchrony threshold comprises a QRS duration with an upper limit of 130 msec.

4. The method of claim 1, further comprising, during delivery of the first series of electrical signals to the atrium of the heart of the user, providing electrical signals to both ventricles of the heart.

5. The method of claim 1, wherein the first series of electrical signals are configured to induce favorable myocardial remodeling of the heart.

6. The method of claim 1, wherein the second series of electrical signals are configured to induce favorable myocardial remodeling of the heart.

7. The method of claim 1, wherein the second series of electrical signals that restores the physiological parameter decreases the second heart rate to a third heart rate.

8. The method of claim 7, further comprising, maintaining the third heart rate with the second series of electrical signals for a time period.

9. The method of claim 1, wherein determining whether the at least two physiological parameters are each within a respective physiological threshold comprises determining whether a third physiological parameter has met a respective physiological threshold.

10. The method of claim 9, wherein the third physiological parameter comprises blood pressure.

11. The method of claim 9, wherein the third physiological parameter comprises respiratory rate.

12. The method of claim 9, wherein the third physiological parameter comprises a bioimpedance measurement of stroke volume.

13. The method of claim 1, further comprising positioning at least one electrode within an esophagus, wherein the at least one electrode is configured to provide the first series of electrical signals.

14. A system comprising:
    a pulse generator configured to deliver a first series of electrical signals to an atrium of a heart wherein the first series of electrical signals increases a first heart rate of the heart toward a target heart rate;
    a monitoring device configured to retrieve physiological data from a user of the system before and while the heart is receiving the first series of electrical signals; and
    a controller comprising:
      a memory comprising computer readable instructions, and
      a processor that, when executing the computer readable instructions, is configured to:
        determine whether at least two physiological parameters are each within a respective physiological threshold based on the physiological data, wherein the at least two physiological parameters comprises an optimal atrio-ventricular synchrony and an optimal interventricular synchrony, wherein the respective physiological threshold of the optimal atrio-ventricular synchrony comprises an atrio-ventricular dyssynchrony threshold, wherein the atrio-ventricular dyssynchrony threshold comprises an atrio-ventricular conduction ratio and an atrio-ventricular delay, and wherein the respective physiological threshold of the optimal interventricular synchrony comprises an interventricular dyssynchrony threshold;

if at least one physiological parameter of the at least two physiological parameters outside of the respective physiological threshold, modify the first series of electrical signals to a second series of electrical signals that restores the at least one physiological parameter to an acceptable level; and if each of the at least two physiological parameters is within the respective physiological threshold, continue delivery of the first series of electrical signals until the target heart rate is met for a target time duration.

15. The system of claim 14, wherein the first series of electrical signals are configured to induce favorable myocardial remodeling of the heart.

16. The system of claim 14, wherein the second series of electrical signals are configured to induce favorable myocardial remodeling of the heart.

17. The system of claim 14, wherein the second series of electrical signals that restore the physiological parameter is configured to decrease the second heart rate to a third heart rate.

18. The system of claim 17, wherein the processor is configured to maintain the third heart rate with the second series of electrical signals for a time period.

19. The system of claim 14, wherein the processor is configured to determine whether a third physiological parameter has met a respective physiological threshold.

20. A method comprising:

analyzing physiologic or symptomatic markers of hemodynamic and symptomatic stability of a heart;

determining a target heart rate for the heart based upon the analysis of hemodynamic and symptomatic stability;

delivering a series of electrical signals to an atrium of the heart, wherein the series of electrical signals increases a heart rate of the heart above a resting heart rate to the target heart rate;

monitoring atrio-ventricular and interventricular synchrony and the heart rate of the heart to ensure atrio-ventricular synchrony at an atrio-ventricular conduction ratio of 1:1 and interventricular synchrony within a predetermined duration while increasing the heart rate to the target heart rate, wherein monitoring the atrio-ventricular synchrony comprises monitoring the atrio-ventricular conduction ratio and an atrio-ventricular delay; and maintaining the heart rate at the target heart rate for a target duration.

* * * * *